(12) United States Patent
O'Keefe et al.

(10) Patent No.: US 7,468,797 B1
(45) Date of Patent: Dec. 23, 2008

(54) ABSORPTION SPECTROSCOPY INSTRUMENT WITH INCREASED OPTICAL CAVITY POWER WITHOUT RESONANT FREQUENCY BUILD-UP

(75) Inventors: Anthony O'Keefe, Cupertino, CA (US); Manish Gupta, Mountain View, CA (US); Thomas G. Owano, Mountain View, CA (US); Douglas S. Baer, Menlo Park, CA (US)

(73) Assignee: Los Gatos Research, Mountain View, CA (US)

( * ) Notice: Subject to any disclaimer, the term of this patent is extended or adjusted under 35 U.S.C. 154(b) by 351 days.

(21) Appl. No.: 11/466,348

(22) Filed: Aug. 22, 2006

Related U.S. Application Data

(60) Provisional application No. 60/761,533, filed on Jan. 24, 2006.

(51) Int. Cl.
*G01N 21/00* (2006.01)

(52) U.S. Cl. ..................................... 356/437; 356/440

(58) Field of Classification Search .................. None
See application file for complete search history.

(56) References Cited

U.S. PATENT DOCUMENTS 6,795,190 B1    9/2004   Paul et al.

*Primary Examiner*—Gregory J Toatley, Jr.
*Assistant Examiner*—Amanda H Merlino
(74) *Attorney, Agent, or Firm*—Schneck & Schneck; Thomas Schneck; Marl Protsik

(57) ABSTRACT

An absorption spectroscopy instrument is provided with a re-injection mirror to greatly increase the optical power coupled into an optical cavity, comprised of two or more mirrors, for the purpose of increasing the quality of absorption and extinction measurements made in the cavity. Light reflected from the first cavity mirror upon which a light beam is incident, can be efficiently collected and back reflected onto the same mirror, effectively producing a plurality of optical injections into the cavity. The instrument can be used for off-axis cavity ringdown spectroscopy, off-axis integrated cavity output spectroscopy, or other cavity-based spectroscopy applications.

23 Claims, 4 Drawing Sheets

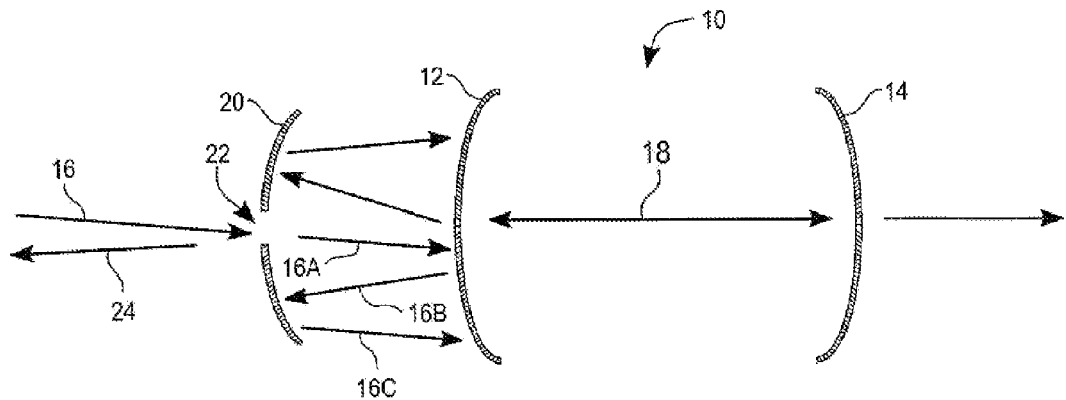
*Fig. \_ 1a*
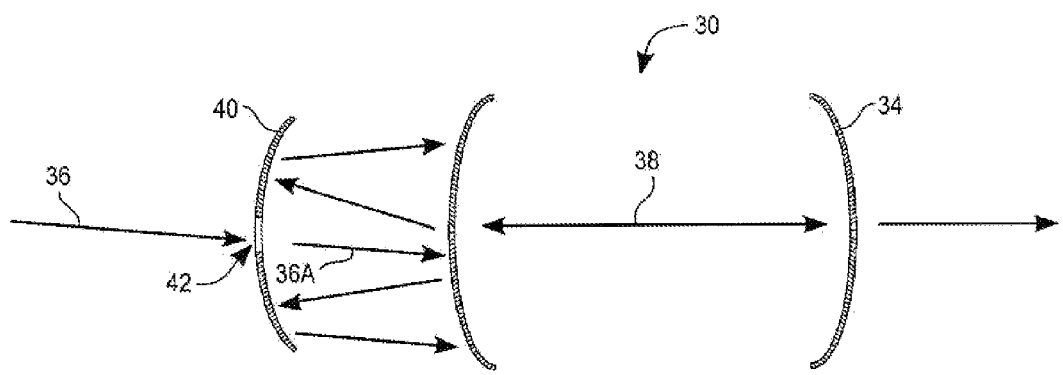
*Fig. \_ 1b*
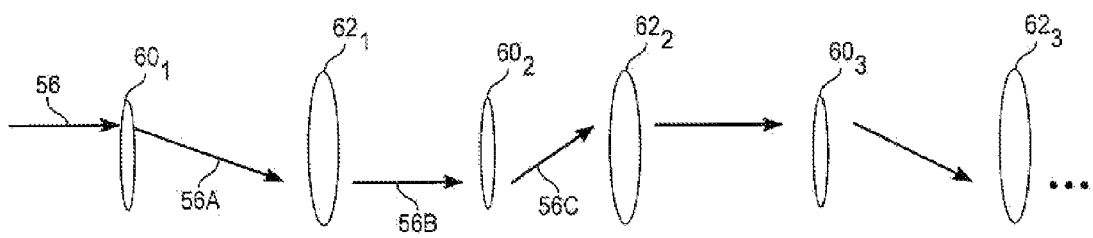
*Fig. \_ 2*

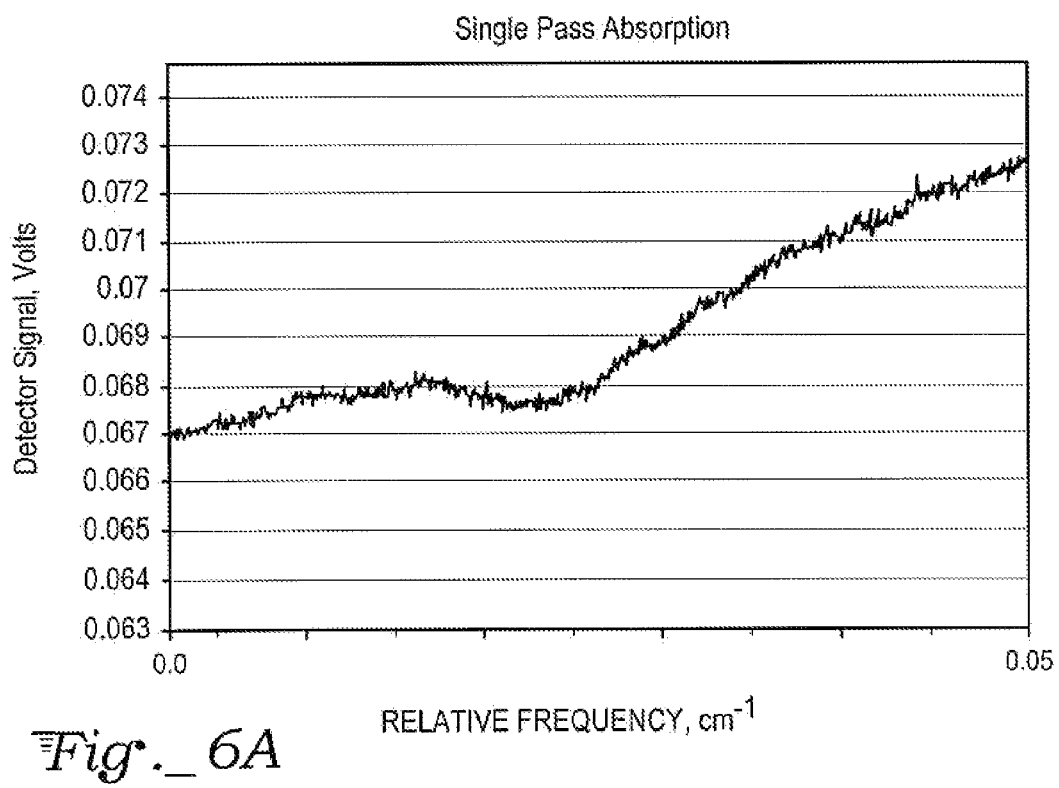
Fig._6A
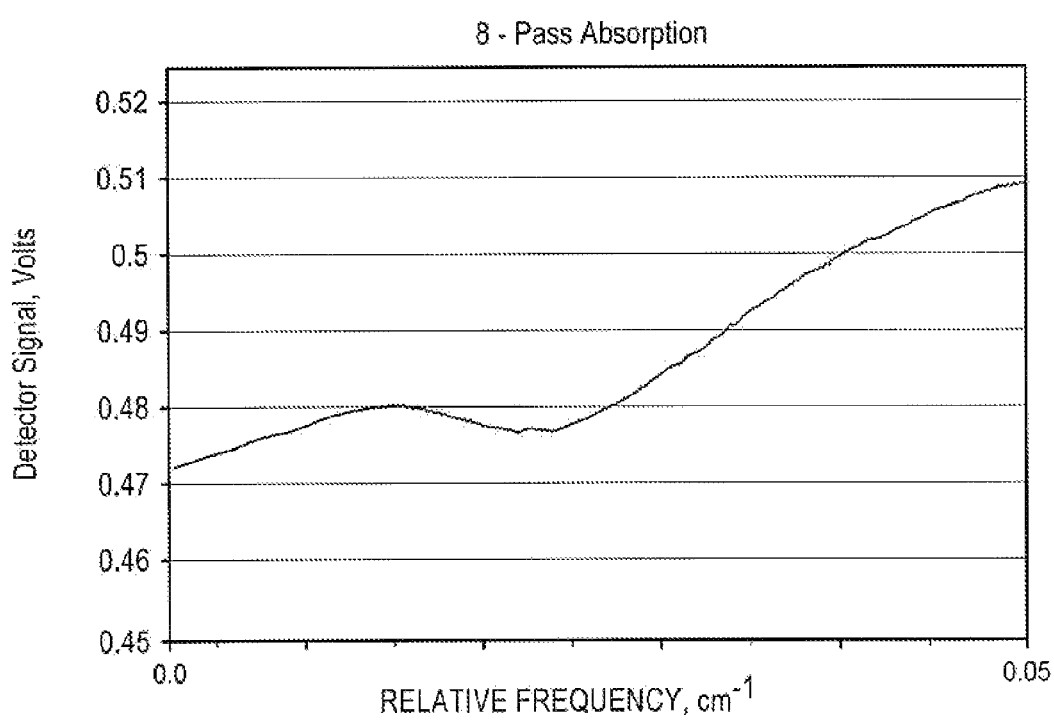
Fig._6B

ABSORPTION SPECTROSCOPY INSTRUMENT WITH INCREASED OPTICAL CAVITY POWER WITHOUT RESONANT FREQUENCY BUILD-UP

CROSS-REFERENCE TO RELATED APPLICATION

This application claims priority under 35 U.S.C. 119(e) from prior U.S. provisional application No. 60/761,533, filed Jan. 24, 2006.

TECHNICAL FIELD

The present invention relates to absorption spectroscopy instruments that employ optical cavities as absorption cells for highly sensitive detection and measurement of trace chemical species, such as those using cavity ringdown spectroscopy (CRDS) and integrated cavity output spectroscopy (ICOS) methods, and especially to spectroscopy instruments that provide off-axis injection of the optical power into the optical cavity.

BACKGROUND ART

It has long been known that high finesse optical cavities amplify optical loss processes occurring between the cavity optics. This cavity amplification ultimately allows highly sensitive measurements of such optical losses to be achieved, e.g., for detecting and determining the concentration of specific chemicals of interest, both at extremely low levels (~ppb) and with very short response times (~µs). Absorption spectroscopy measurements of this kind are useful for a variety of applications, including pollution monitoring, toxic chemical detection, process control monitoring, off-gas monitoring, trace gas analysis, purity analysis, and medical diagnostics (e.g., breath analysis).

Several methods for using optical cavities for these purposes have been described. One of the most common cavity-based spectroscopic methods is known as cavity ringdown spectroscopy (CRDS). Radiation is injected into an optical cavity, either by a single laser pulse or by an abruptly interrupted continuous-wave (CW) laser, which has been chosen to match an absorption wavelength of an atomic or molecular species of interest. A photodetector measure total intra-cavity loss by observing the exponential decay over time of the output intensity following the radiation injection. The time constant of the decay depends upon all losses in the cavity, including losses due to chemical absorption, with stronger absorption producing a faster decay rate. Intrinsic losses can be isolated by measuring the decay rate in the absence of any chemical absorbers.

Other methods, such as integrated cavity output spectroscopy (ICOS) and noise-immune cavity-enhanced optical heterodyne molecular spectroscopy (NICE-OHMS), use cavity transmission properties to gauge the intra-cavity loss. ICOS is similar to CRDS, but does not involve pulsing or blocking of the laser light or measuring the cavity decay rate. Instead, continuous light injection is used, and the intra-cavity intensity builds to a saturation value determined by the cavity mirror reflectivity and the sample absorption. In these cases, the intrinsic cavity loss may be determined separately, by suing CRDS for example, to obtain quantitative absorption intensity data. Light trapped in the optical cavity passes through the absorbing sample many times, so the observed amplification of the absorption signal is very large (typically on the order of 100 to 10000).

Most of these methods in some way manipulate the optical resonances that arise in the cavity due to the periodic boundary conditions imposed on the intra-cavity electric field by the mirror surfaces. These resonances, which are interferometric in nature, comprise the general subject of Fabry-Perot theory. To precisely control the resonances generally requires complex and expensive instrumentation and hardware, and places extreme constraints on the overall stability of the apparatus.

In a typical version of ICOS, the system may be dithered, in which the laser's wavelength is rapidly modulated over a frequency spacing containing several cavity modes, or in which one of the cavity mirrors is rapidly vibrated with a piezoelectric transducer to oscillate the cavity length, or both. This forced rapid randomization of cavity modes allows the cavity output intensity to be averaged to within $\Delta I/I_0$-$10^{-2}$ or better.

More recently, two off-axis techniques, known as Off-Axis Cavity Ringdown (oa-CR) and Off-Axis ICOS (oa-ICOS), have been developed that introduce the light into the optical cavity along an off-axis light path so as to systematically disrupt optical resonances and remove the frequency selectivity of the cavity, thereby rendering it effectively a broadband device. As a result, narrowband lasers (bandwidth $\Delta v < 100$ MHz) can be used without activity controlling the cavity length. This eliminates the need for expensive components such as acousto-optic modulators, piezoelectric transducers, lock-in amplifiers, etc. This design also reduces optical feedback from the cavity into the source laser, which is particularly important for the case of a distributed-feedback diode laser as the source laser. Previously, either expensive Faraday isolators or three-mirror ring-cavities have been used for this purpose. Additionally, the constraints on the overall system alignment are vastly reduced. Rather than having only one possible alignment geometry (i.e., the laser on-axis with the cavity), any of the many stable paths through the cavity can be used. This allows faster alignment routines, and lowers the sensitivity of the instrument to vibration. Coupled with a slight astigmatism (optional) of the cavity mirrors, the off-axis light path increases the beams's reentrant condition from a single pass (for standard ICOS) to almost 1000 passes, which well exceeds the coherence length of the laser light. As a result, the cavity's output intensity can be effectively averaged to within $\Delta I/I_0 \sim 10^{-4}$.

A drawback of the off-axis geometry is that, since none of the resonant cavity frequency modes are preferentially populated, no appreciable power build-up occurs inside the optical cavity. This results in a net reduction in the transmitted power by a factor of T/2, where T is the average cavity mirror transmission. This power reduction can be very significant, since T is on the order of $10^{-4}$ to $10^{-5}$ for mirrors typically used in such applications, meaning that in applications employing a milliwatt laser, the detector will measure only 10-100 nanowatts of power. Many potentially interesting applications of these off-axis techniques that would employ weak laser sources, such as cryogenic lead-salt diode lasers, or even non-laser sources, are not practical since the signal on the detector would be too low to be useful. Thus, a way to greatly increase the amount of optical power that can be injected off-axis into an optical cavity would improve the applicability of the oa-CR and oa-ICOS techniques.

SUMMARY DISCLOSURE

The present invention is an optical cavity-based absorption spectroscopy instrument in which that portion of the light from a source that initially fails to couple into the optical cavity is repeatedly collected and re-injected until it successfully couples into the cavity. This repeated injection effectively increases the net optical power coupled into the cavity and eliminates the problem of low light levels in existing off-axis designs.

An oa-CR or oa-ICOS system in accord with this invention utilizes multiple reflections of the injection optical beam back onto the off-axis cavity mirror. Because the cavity mirror reflectivity is nearly unity, the light reflected from the cavity mirror and thereby failing to couple into the optical cavity is only slightly decreased in amplitude from the previous injection attempt. A re-injection mirror is positioned to collect this light and reflect it back toward the off-axis cavity mirror. With a suitable choice of the optical parameters, a large number of back reflections can be produced. After a large number of repeated injections of the input light, we can effectively multiply the coupling efficiency of the input light by a factor of from 2 to several orders of magnitude.

BRIEF DESCRIPTION OF THE DRAWINGS

FIG. 1A is a schematic diagram of a first embodiment in accord with the present invention, wherein the input injection light beam passes through a small hole in the re-injection mirror.

FIG. 1B is a schematic diagram of a second embodiment in accord with the present invention, wherein the input injection light beam passes through a small region of reduced reflectivity on the re-injection mirror face.

FIG. 2 shows an equivalent lens series diagram used to model the re-injection cavity optical ray path evolution for the embodiments of FIGS. 1A and 1B.

FIGS. 6A and 6B are oa-ICOS signals taken of a weak absorption $CO_2$ feature using, respectively, a comparable prior art single-injection oa-ICOS design and using a multi-injection oa-ICOS design of the present invention, illustrating approximately 10-fold improvement in signal-to-noise ratio.

DETAILED DESCRIPTION

Figure 3:
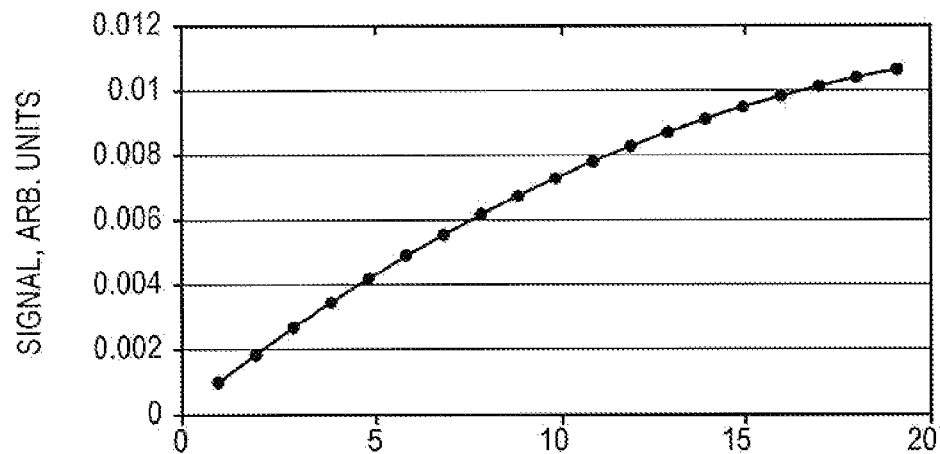
FIG. 3 is a graph of the theoretical intra-cavity power (arbitrary units) as a function of the number of re-injections for an arrangement as shown in either FIG. 1A or 1B.

Absorption spectroscopy instruments in accord with the present invention offer improved injection of optical power into the cavity, so that weaker light sources than those previously practicable are now possible. Many kinds of light source may be used, not limited only to lasers, but also including atomic and molecular lamps, or other non-coherent broad-spectrum sources. The lasers may be tuned over a wavelength range of interest, and the lamps and other broad-spectrum sources may be wavelength-filtered to sequentially select a set of desired wavelengths corresponding to an absorption band of a chemical species of interest. If broad-spectrum detection is available, via a spectrometer, then the broad-spectrum source need not be filtered and absorption at all wavelengths in a band of interest can be sampled and measured simultaneously.

Absorption spectroscopy instruments of the present invention may be of the oa-ICOS or oa-CR type. In the oa-ICOS case, the light source provides an uninterrupted, substantially constant intensity light beam to the optical cavity so as to obtain an oa-ICOS absorption signal from an intensity measurement by a photodetector of light extracted from the cavity. In the oa-CR case, the light source includes means for pulsing, intensity modulating, or chopping the light provided to the optical cavity in a manner designed to obtain an oa-CR absorption signal measurement from the intensity decay rate of the cavity output light received by the photodetector. For example, the light source may have a modulated drive current input resulting in modulated output power from the source. Various chopping elements are available for placement in the path of a continuous beam, such as mechanical choppers, acousto-optic modulators and electro-optic modulators. Whatever its origin, the light beam provided in an oa-CR instrument should have an intensity fall time that is substantially shorter than the ringdown time, while the repetition cycle time should be longer than the ringdown time.

Other known elements of an absorption spectroscopy instrument that are used substantially as in previous device include the photodetector, which is situated in a position to receive a portion of the light beam extracted from the optical cavity, e.g., through one of the cavity mirrors. A data processing system processes the light measurements from the detector in a known manner to obtain absorption values over a range of wavelengths, and may provide further analysis of the sample. The cavity itself is adapted to receive an absorption cell with a sample to be tested. The term "absorption cell" is used loosely to refer to any arrangement for introducing the sample into light paths in the optical cavity. For example, a low-scatter sample flow configuration may be provided in which the gas flow passes through a plurality of off-axis light paths of the cavity for absorption measurement of trace chemical species in the gas sample.

A feature of the present invention relates to improvements in successfully injecting optical power from the source into the optical cavity, a detailed description of which follows. An arrangement of two or more mirrors forms a stable optical cavity, and the light beam from the source will be coupled into the cavity along off-axis light paths thereof. The cavity mirrors may be planar, or have spherical or astigmatic curved reflecting surfaces, or some combination thereof. The cavity mirrors may be separated from each other by any selected distance greater than or equal to that for a confocal cavity arrangement and less than that for a concentric cavity arrangement. However, whatever cavity is chosen, the light is injected into the cavity through one of the cavity mirrors, referred to for convenience as the "first" cavity mirror. The cavity mirrors are highly reflective, i.e., have a normal reflectivity at the source wavelength of at least 99%, and more typically greater than 99.9%, e.g. 99.99%, in order to minimize intrinsic losses. This means that transmission of light through the first cavity mirrors is extremely low. The first cavity mirror reflects a large portion of the source light beam, so that this portion initially fails to couple into the cavity.

With reference to FIGS. 1A and 1B, the optical cavity 10 or 30 is defined by a pair of cavity mirrors 12 and 14 (or 32 and 34 in FIG. 1B). If desired, a ring cavity with more than two mirrors can be used. The cavity mirrors can have any curvatures and positions that create a stable optical cavity. The initial light beam 16 from a light source can pass through a small hole 22 or a region 42 of reduced reflectivity in the re-injection mirror 20 or 40. Some fraction of the light 16A or 36A passing through the hole 22 or region 42 and directed upon the first cavity mirror 12 or 32 will couple into the optical cavity 10 or 30. The remaining uncoupled portion will be reflected back by the first cavity mirror 12 or 32, where it can be collected and redirected by the re-injection mirror 20 or 40.

The hole 22 or region 42 in the re-injection mirror 20 or 40 is small, typically less than 5 mm diameter, so that it represents a tiny portion (not typically more than about 1%) of the total mirror area. At the same time, it must be large enough to allow the light beam 16 to pass. The remainder of the re-injection mirror 20 or 40 typically has a reflectivity greater than 90%. A higher reflectivity for the re-injection mirror 20 or 40 permits more of the light to be collected and redirected back toward the cavity, and hence improves overall coupling of the light into the optical cavity 10 or 30. However, the mere presence of a re-injection mirror 20 or 40 of any reflectivity level will enhance coupling of the available optical power into the optical cavity 10 or 30.

In the first design (small hole) seen in FIG. 1A, the light beam 16, after passing through the hole 22, will undergo a series of reflections between the cavity mirror 12 and the re-injection mirror 20. The light 16A, 16B, 16C, etc. in the re-injection space will either couple through the mirror 12 into the optical cavity 10 or will eventually pass back out 24 through the hole 22 in the re-injection mirror 20. This results in a finite number of re-injections, typically at most several hundred.

In the second design (reduced reflectivity region) seen in FIG. 1B, the initial light beam is reduced in amplitude by passage through the partially reflecting region 42, where the reflection can range from a fraction of a percent to nearly 100 percent. The partially transmitted light 36A will undergo a series of reflections between the cavity mirror 32 and the re-injection mirror 40. Since there is no hole in the mirror 40, the beam is effectively trapped in a closed pattern, limited only by losses from transmission through the two mirrors, especially where the beam reencounters the partially reflecting region 42 in the re-injection mirror 40.

In both of the two cases described above: 1) the curvature of the "re-injection mirror" 20 or 40 is greater than that of the input cavity mirror 12 or 32 so that the reflected beams are efficiently trapped; 2) the re-injection mirror 20 or 40 has a diameter, or reflective aperture, that is at least as large as that of the input cavity mirror 12 or 32; and 3) the re-injection mirror 20 or 40 is positioned along the cavity axis at a distance from the input cavity mirror 12 or 32 such that the typical angle of injection for each reflected beam has a beam waist near, or at, the center of the optical ICOS or CRD cavity 10 or 30.

The last condition requires the re-injection mirror 20 or 40 to be no further than its focal length from the cavity injection mirror 12 or 32, although since the light beams that reach the re-injection mirror are diverging, the exact distance can vary with initial conditions. The combination of the re-injection mirror 20 or 40 and the backside of the optical cavity input mirror 12 or 32 comprise a second optical cavity containing both a positive and negative mirror. The optical system can be modeled using the ray propagation equations as described in Yariv ["Optical Electronics," Holt, Rinehart, and Winston, 1985]. Light contained within this cavity (FIGS. 1A and 1B) can be modeled as the equivalent repeating lens waveguide (FIG. 2). In FIG. 2, the successive encounters of the light 56 with the re-injection mirror 20 or 40 (FIGS. 1A and 1B) are represented as equivalent lenses $60_1$, $60_2$, $60_3$, etc. The encounters of the light 56 with the first cavity mirror 12 or 32 are represented as equivalent lenses $62_1$, $62_2$, $62_3$, etc. The affected light beams 56A, 56B, 56C, etc. correspond to the light beams 16A, 16B, 16C in FIG. 1A, and similar beams 36A, etc. in FIG. 1B. The position and direction of a given optical ray upon passage through such an optical element array is, after s elements, $$r0 := \begin{bmatrix} x \\ Sx \\ y \\ Sy \end{bmatrix}, \quad TR1 := \begin{bmatrix} 1 & 0 & 0 & 0 \\ \frac{-2}{R1} & 1 & 0 & 0 \\ 0 & 0 & 1 & 0 \\ 0 & 0 & \frac{-2}{R1} & 1 \end{bmatrix},$$

$$TL := \begin{bmatrix} 1 & L & 0 & 0 \\ 0 & 1 & 0 & 0 \\ 0 & 0 & 1 & L \\ 0 & 0 & 0 & 1 \end{bmatrix}, \quad TR2 := \begin{bmatrix} -1 & 0 & 0 & 0 \\ \frac{2}{R2} & 1 & 0 & 0 \\ 0 & 0 & 1 & 0 \\ 0 & 0 & \frac{-2}{R2} & 1 \end{bmatrix}$$

where t(i) is the spot position made by the ray after i passes in the cavity, L is the distance between elements (assumed to be equal to 30 cm in this embodiment), and R1/2 and R2/2 are the focil of the two types of mirrors (or focal lengths of the equivalent lenses) that comprise the array.

The radius of curvature of the re-injection mirror is greater than the distance between the re-injection mirror and the first test cavity mirror. The radius of curvature of the re-injection mirror is less than or equal to that of the average (geometric mean) of the test cavity mirrors' radii of curvature, i.e., $R_{re} \leq \sqrt{(R2 * R2)}$ for a two-mirror cavity (e.g., mirrors 12 and 14 in FIG. 1A, or mirrors 32 and 34 in FIG. 1B).

The optical cavity formed by the re-injection mirror and the input mirror to the sample cavity is a combination of a positive and negative mirror, or a positive mirror and a flat mirror, since the sample cavity mirror is usually either focusing into the cavity or flat. (NOTE: it is clear that the sample cavity could also be made up of a positive and negative mirror. In this case, the re-injection cavity is a stable positive-positive case.) In the case of a positive-negative mirror combination, the ray matrix equation changes with a change in the sign of the second focal length.

The transmitted power through the ICOS sample cell was monitored using a photomultiplier tube as the number of spots seen in the re-injection cavity was varied by manually blocking reflections. This provides a measure of the injected power for one spot, two spots, four spots, eight spots, and the maximum number of spots that could be attained using the metal re-injection mirror.

The predicted transmitted power can be easily calculated by summing the finite number of reflected re-injections and consideration of the decreased re-injection power due to the reflectivity losses of a metal mirror, R≈93%. The sample ICOS cell mirror is highly reflecting (normal reflectivity at the source wavelength ~0.9999) and can be considered as a 100% reflecting mirror. FIG. 3 plots the predicted transmitted power (arbitrary units) as a function of the number of re-injections, or the number of spots observed on the re-injection mirror when aligned as described. The incremental increase drops off since the re-injection mirror has a finite reflectivity. If the re-injection mirror had a reflectivity of better than 0.999, the plot would show almost no drop off and would appear linear.

Figure 4:
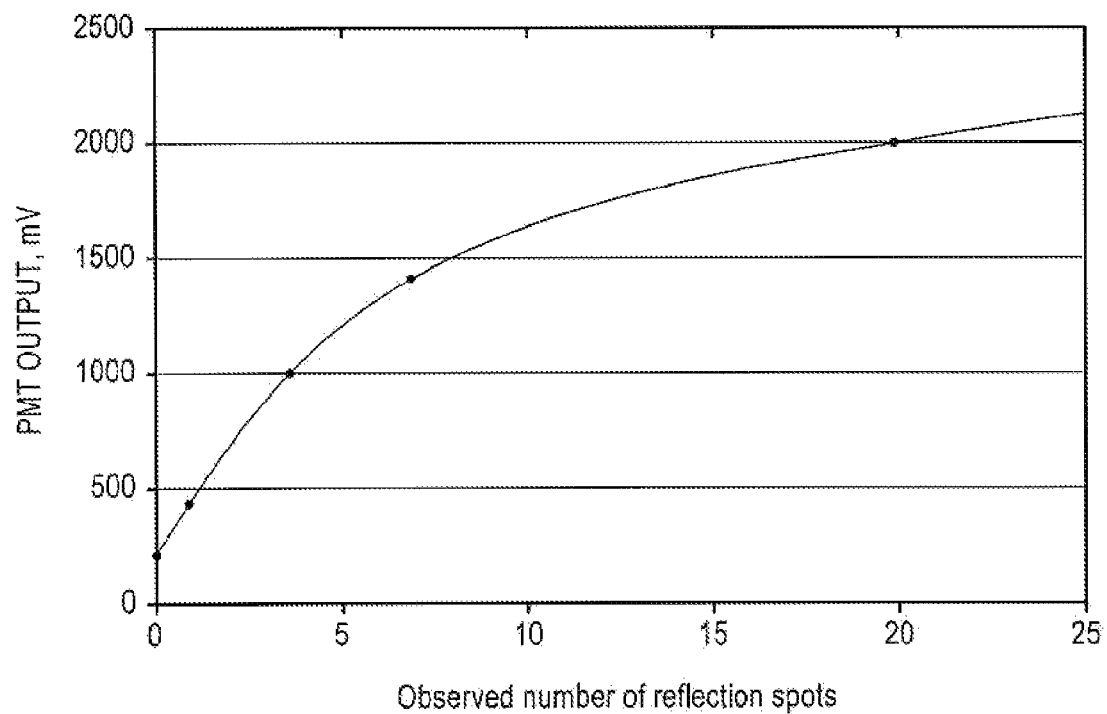
FIG. 4 is a graph of the measured optical cavity transmission signal (in mV) versus the number of re-injection light spots seen on the input ICOS cell mirror.

FIG. 4 plots the measured transmitted power (photomultiplier tube output in millivolts) for different numbers of re-injections. The cavity mirrors had curvatures of 5 m, and the re-injection mirror had a curvature of 1 m and was located 20-30 cm from the cavity injection mirror. The number of spots was adjusted by adjusting the re-injection mirror alignment, as well as by manually blocking successive reflection paths between the mirrors to vary the number of optical re-injections. The increase in measured cavity transmission is very similar to that of the predicted curve (FIG. 3). There is growing uncertainty in the number of reflected spots as this number increases due to overlap of the spots. The number of re-injections corresponding to the maximum transmission is estimated to be ~20.

Measurements of off-axis ICOS absorption of weak $CO_2$ combination band transitions compare the single injection oa-ICOS performance to the multi-injection oa-ICOS performance. In these tests, the oa-ICOS cavity was 60 cm long and employed 2-inch diameter mirrors, each with a 1-meter radius of curvature. The reflectivity of these mirrors at the test wavelength was approximately 99.99%. The re-injection mirror in this embodiment was a 2-inch diameter aluminum high-reflection-coated concave mirror with a 60 cm radius of curvature. The re-injection mirror was located 10 cm from the oa-ICOS cavity input mirror. The re-injection mirror had a small 2 mm hole drilled through the coating that opened into a larger 5 mm bore that extended to the rear face of the mirror substrate. This design permitted a range of optical alignments through the re-injection mirror, and permitted the re-injection mirror to be tilted with respect to the cavity axis. The injection hole was offset from the center of the mirror to align with the standard oa-ICOS geometry.

With the laser aligned to the oa-ICOS cell, the re-injection mirror is set in place and aligned so that the base-line transmission signal measured by the detector behind the oa-ICOS cell is increased. The variation in this measured signal is due to a variation in the number of stable re-injection trajectories into the oa-ICOS cavity.

Figure 5A:
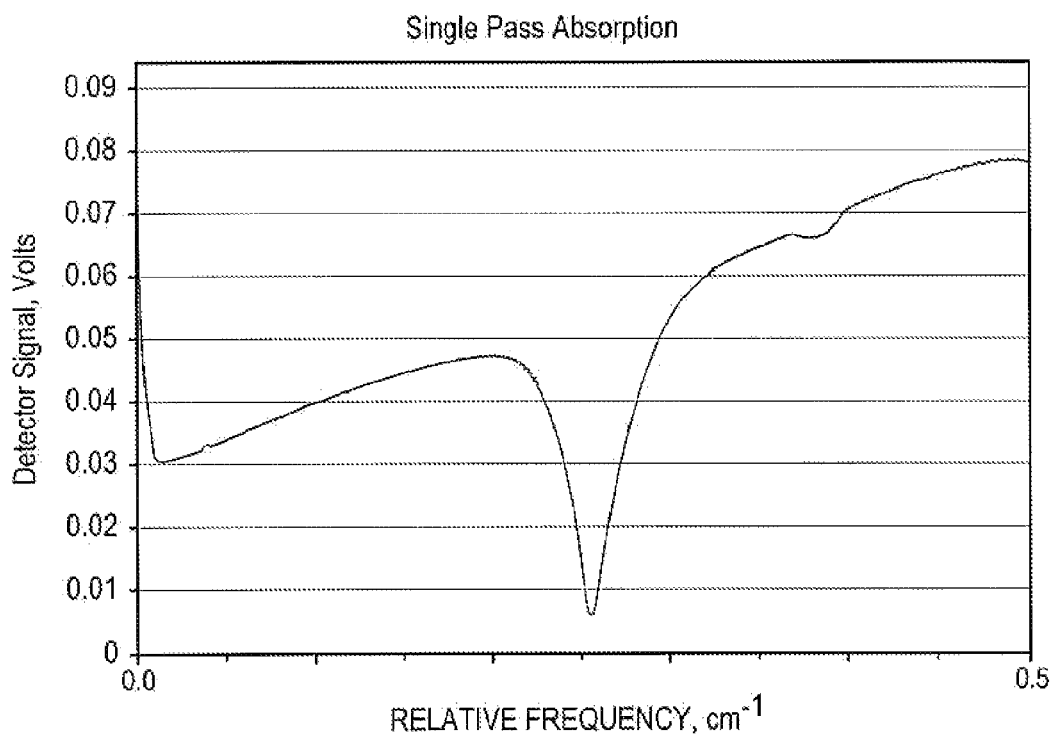
FIGS. 5A and 5B are absorption spectra of a weak $CO_2$ line near 1.57 μm wavelength for, respectively, a comparable prior art single-injection oa-ICOS design and a multi-injection oa-ICOS design of the present invention.
Figure 5B:
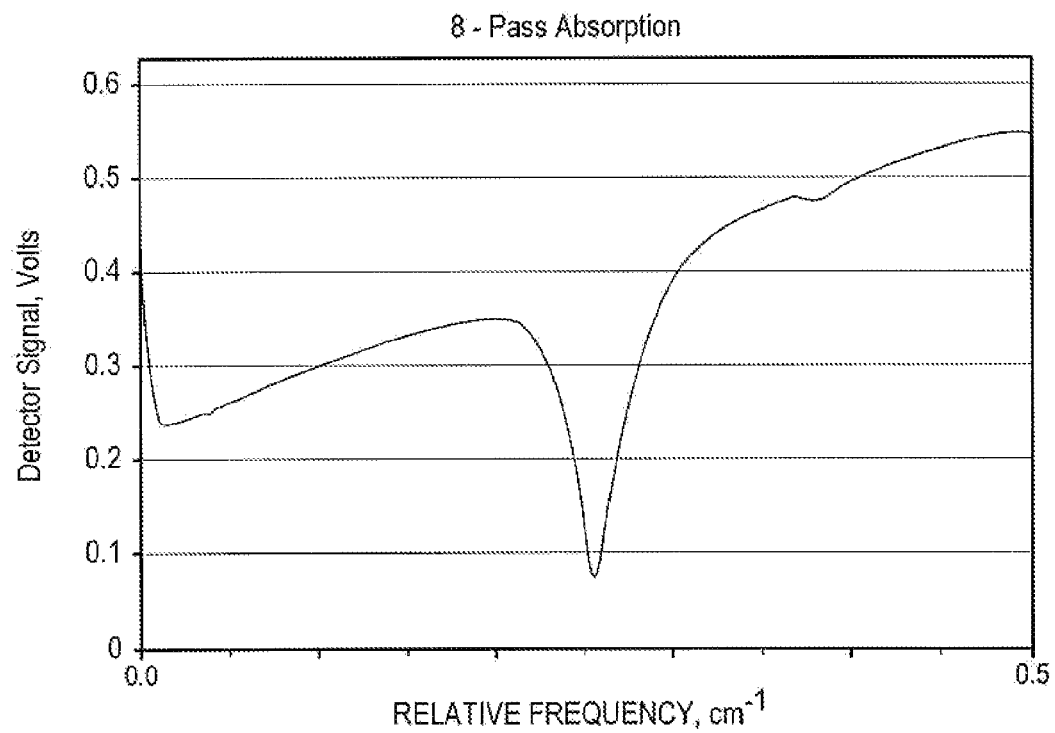

FIGS. 5A and 5B show measured oa-ICOS absorption spectra obtained, respectively, with the re-injection mirror removed (single-injection) and in place (multi-injection) per the present invention. Using ambient levels of $CO_2$ in room air at a reduced pressure of ~30 Torr, the $CO_2$ lines seen are weak lines near 1.57 µm. The figures show the sloping base line of the laser transmission signal with the absorption seen as the sharp decrease in the signal in the middle of the trace. The amplitude of the signal, as seen in the Y-axis value, is more than 7 times greater in FIG. 5B (the re-injection case) than in FIG. 5A, demonstrating the increase in injected power achieved using this scheme. Alignments are possible that offer greater than a nine-fold increase in the total injected power.

A blow-up of the weak absorption feature seen near point 7800 to demonstrates that the increase in signal amplitude is also accompanied by an increase in the signal to noise (S/N) evident in FIGS. 6A and 6B. FIG. 6A shows the single injection result and FIG. 6B shows the multi-injection result. The resulting improvement in S/N ratio is approximately a factor of 7.

The use of astigmatic mirrors further increases the number of re-injections before the optical beam exits the hole in the re-injection mirror. It should be possible to use other than spherically shaped mirrors, including parabolic, segmented, and flexible surface mirrors. A ring cavity design with more than two mirrors forming the re-injection cavity is also possible.

The approach can also be used in cavity ringdown spectroscopy (CRDS) and off-axis cavity ringdown (oa-CR) spectroscopy, as long as the effective optical residence time in the weak cavity formed by the re-injection mirror and the first test cavity (oa-ICOS cavity in our example) mirror is short compared to that of the test cavity. If the re-injection mirror reflectivity is very high, and if there are many passes of the light between the re-injection mirror and the test cavity mirror, the measured ringdown time would be distorted.

What is claimed is:

1. A absorption spectroscopy instrument, comprising:
   an arrangement of two or more mirrors forming a stable optical cavity that is adapted to receive an absorption cell with a sample to be tested, the arrangement of mirrors defining both an axial light path in the cavity and a plurality of off-axis light paths in the cavity wherein successive reflections at any given mirror of the cavity occur at different locations for any of the off-axis light paths;
   a light source providing a light beam directed toward a first cavity mirror, a first portion of the light beam being coupled by transmission through the first cavity mirror into the cavity along an off-axis light path, and a second portion of the light beam being reflected back by the first cavity mirror and thereby initially failing to be coupled into the cavity;
   a re-injection mirror situated between the light source and the first cavity mirror and configured to collect and redirect the reflected second portion of the light beam back toward the first cavity mirror for one or more additional attempts to couple the second portion of the light beam into the cavity;
   a detector situated in a position to receive and measure another portion of the light beam extracted from the optical cavity through a second cavity mirror; and
   means for processing data representing the light measurement from the detector for analyzing a sample in said absorption cell.

2. The instrument as in claim 1, wherein the cavity mirrors have reflectivities greater than 99%.

3. The instrument as in claim 1, wherein the re-injection mirror has a reflectivity greater than 90%.

4. The instrument as in claim 1, wherein the re-injection mirror has a hole therein through which the light beam from the light source may initially pass on its way to the first cavity mirror.

5. The instrument as in claim 1, wherein the re-injection mirror has a region of reduced reflectivity through which the light beam from the light source may initially pass on its way to the first cavity mirror.

6. The instrument as in claim 1, wherein the re-injection mirror has a diameter at least as great as the first cavity mirror.

7. The instrument as in claim 1, wherein the re-injection mirror is more greatly curved than the first cavity mirror.

8. The instrument as in claim 1, wherein the re-injection mirror is positioned at a distance from the first cavity mirror such that the redirected second portions of the light beam from the re-injection mirror when coupled through the first cavity mirror into the cavity have a beam waist located within the cavity and substantially coinciding with a cavity-defined beam waist location for stable propagation.

9. The instrument as in claim 8, wherein the re-injection mirror is positioned at a distance of not more than a focal length of that re-injection mirror.

10. The instrument as in claim 8, wherein the re-injection mirror has a radius of curvature that is greater than the distance between the re-injection mirror and the first cavity mirror, but is also less than or equal to a geometric mean of the radii of curvature of the cavity mirrors.

11. The instrument as in claim 1, wherein the cavity mirrors are separated from each other by a distance greater than or equal to a confocal cavity arrangement but less than a concentric cavity arrangement.

12. The instrument as in claim 1, wherein at least one cavity mirror has a spherical reflecting surface curvature.

13. The instrument as in claim 1, wherein at least one cavity mirror has an astigmatic reflecting surface curvature.

14. The instrument as in claim 1, wherein the light source is a wavelength tunable laser.

15. The instrument as in claim 1, wherein the light source is an atomic or molecular lamp.

16. The instrument as in claim 1, wherein the light source is an light-emitting diode.

17. The instrument as in claim 1, wherein the light source provides an uninterrupted, substantially constant intensity light beam to the optical cavity so as to obtain an off-axis integrated-cavity-output spectroscopy absorption signal from the light measurement of the detector.

18. The instrument as in claim 1, wherein the light source includes means for pulsing, intensity modulating, or chopping the light beam provided to the optical cavity in a manner designed to obtain an off-axis cavity ringdown spectroscopy absorption signal measurement from a decay rate of the light received by the detector.

19. The instrument as in claim 1, wherein the absorption cell is a low-scatter sample gas flow arrangement passing through the plurality of off-axis light paths of the optical cavity for measurement of trace chemical species in a gas sample.

20. An absorption spectroscopy method, comprising:
providing an arrangement of mirrors forming a stable optical cavity;
receiving a sample to be tested in the optical cavity;
directing a light beam from a light source onto a first of the mirrors of the optical cavity for coupling through that first cavity mirror into the optical cavity along an off-axis path, only a first portion of the light beam from the light source initially coupling into the cavity, while a remaining second portion of the light beam is reflected back by the first cavity mirror;
providing a re-injection mirror outside of the optical cavity in a position selected to collect the reflected second portion of the light beam and to redirect that second portion back onto the first cavity mirror for further coupling of the redirected light into the optical cavity, the re-injection mirror provided with a passage for the light beam from the light source on its way to the first cavity mirror;
measuring light from the optical cavity; and
processing light measured data to obtain an analysis of absorption by the sample received in the optical cavity.

21. The method as in claim 20, wherein the re-injection mirror and the first cavity mirror have curvatures and relative positions selected to effectively form a second stable optical cavity.

22. The method as in claim 20, wherein the means for allowing passage of the light beam from the light source comprises a hole in the re-injection mirror.

23. The method as in claim 20, wherein the means for allowing passage of the light beam from the light source comprises a region of lower reflectivity in the re-injection mirror.

* * * * *

UNITED STATES PATENT AND TRADEMARK OFFICE
CERTIFICATE OF CORRECTION

| | | |
|---|---|---|
| PATENT NO. | : 7,468,797 B1 | Page 1 of 1 |
| APPLICATION NO. | : 11/466348 | |
| DATED | : December 23, 2008 | |
| INVENTOR(S) | : Anthony O'Keefe et al. | |

It is certified that error appears in the above-identified patent and that said Letters Patent is hereby corrected as shown below:

Column 2, lines 15-16, "...averaged to within $\Delta I/I_0$ - $10^{-2}$ or better." should read --...averaged to within $\Delta I/I_0 \approx 10^{-2}$ or better.--.

Column 6, lines 23-24, "...are the focil of the two types of mirrors..." should read --...are the focii of the two types of mirrors--.

Signed and Sealed this

Seventh Day of April, 2009

JOHN DOLL
*Acting Director of the United States Patent and Trademark Office*